US00PP34218P2

(12) United States Plant Patent
Bergman

(10) Patent No.: US PP34,218 P2
(45) Date of Patent: May 10, 2022

(54) ***LANTANA* PLANT NAMED 'LANZ0039'**

(50) Latin Name: *Lantana camara L.*
Varietal Denomination: LANZ0039

(71) Applicant: SYNGENTA CROP PROTECTION AG, Basel (CH)

(72) Inventor: Wendy R. Bergman, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 17/362,000

(22) Filed: Jun. 29, 2021

(51) Int. Cl.
*A01H 5/00* (2018.01)
*A01H 6/86* (2018.01)

(52) U.S. Cl.
USPC ..... Plt./227

(58) Field of Classification Search
USPC ..... Plt./226, 227
See application file for complete search history.

*Primary Examiner* — Susan McCormick Ewoldt
*Assistant Examiner* — Karen M Redden
(74) *Attorney, Agent, or Firm* — Dale Skalla

(57) ABSTRACT

A new *Lantana* plant named 'LANZ0039' having medium size mature orange flowers, excellent flower production, vigorous plant growth and uniform dense semi-spreading habit with medium sized dark green foliage and very little seed set.

1 Drawing Sheet

Latin name of the genus and species of the plant claimed: *Lantana camara L.*

Varietal denomination: 'LANZ0039'.

BACKGROUND OF THE NEW PLANT

The present invention comprises a new *Lantana*, botanically known as *Lantana camara L.,* and hereinafter referred to by the variety name 'LANZ0039'.

'LANZ0039' is a product of a planned breeding program in Gilroy, Calif. The new cultivar 'LANZ0039' has medium size mature orange flowers, excellent flower production, vigorous plant growth and uniform dense semi-spreading habit with medium sized dark green foliage.

The new *Lantana* cultivar, 'LANZ0039', is the result of cross-pollination made in Gilroy, Calif. in August 2016. The female parent of the new cultivar is the proprietary *Lantana camara* breeding selection 'H0030-1', not patented, characterized by its orange inflorescences, medium green-colored foliage and vigorous spreading growth habit. The male parent of the new cultivar is 'LANZ0032', U.S. Pat. No. 32,225, characterized by its yellow flowers, compact mounding growth habit and medium green foliage.

The seed was sown in December 2016 in a controlled greenhouse environment in Gilroy, Calif., and 'LANZ0039' was selected as one flowering plant within the progeny of the stated cross in April 2017.

The first act of asexual reproduction of 'LANZ0039' was accomplished when vegetative cuttings were propagated from the initial selection in July 2017 in Gilroy, Calif.

BRIEF SUMMARY OF INVENTION

Horticultural examination of plants grown from cuttings of the plant initiated in July, 2017, in Gilroy, Calif., and continuing thereafter, has demonstrated that the combination of characteristics as herein disclosed for 'LANZ0039' are firmly fixed and are retained through successive generations of asexual reproduction.

'LANZ0039' has not been observed under all possible environmental conditions. The phenotype may vary significantly with variations in environment such as temperature, light intensity, and day length.

A Plant Breeder's Right for this cultivar has not yet been applied for. 'LANZ0039' has not been made publicly available prior to the effective filing date of this application, notwithstanding any disclosure that may have been made less than one year prior to the effective filing date of this application by the inventor or another who obtained 'LANZ0039' directly from the inventor.

The following traits have been repeatedly observed and are determined to be basic characteristics of the new variety. The combination of these characteristics distinguishes this *Lantana* as a new and distinct variety.

BRIEF DESCRIPTION OF THE PHOTOGRAPHS

The accompanying photographic drawings, taken in September 2020, show typical flower and foliage characteristics of 'LANZ0039' with colors being as true as possible with an illustration of this type.

Figure 1:
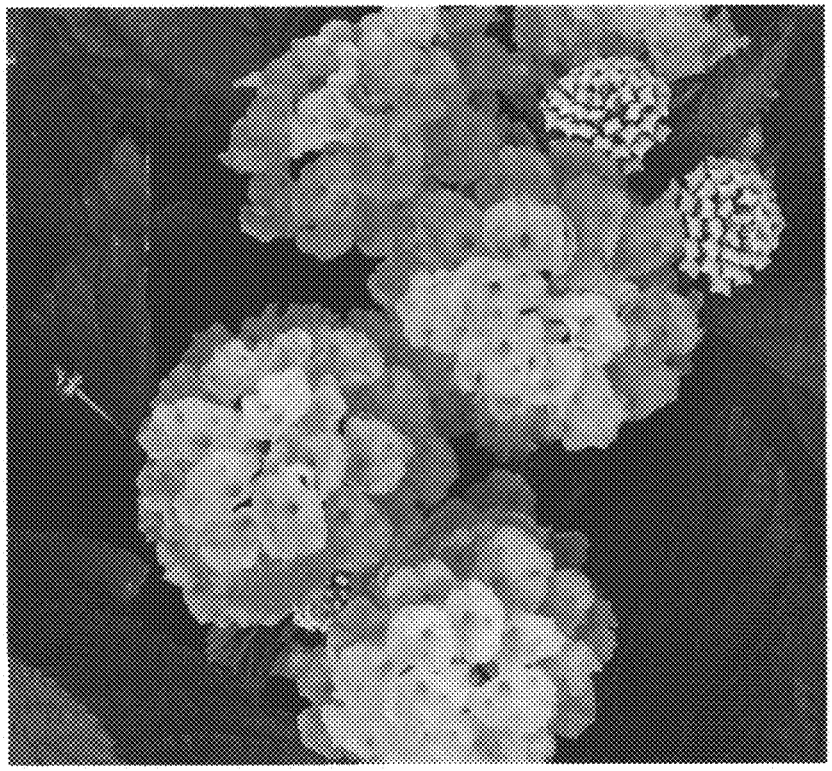
Figure 2:
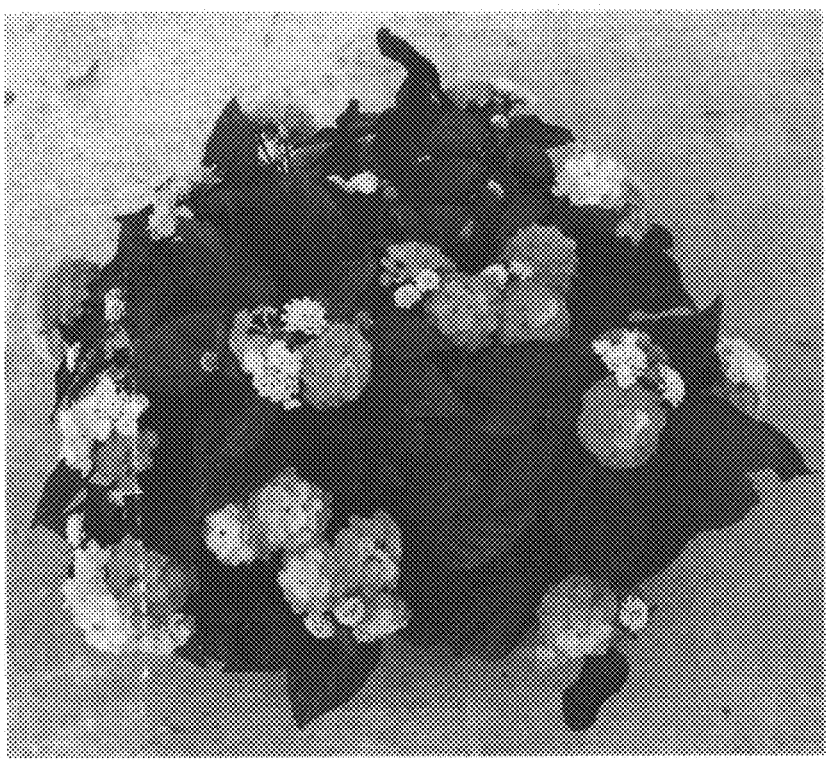

The photographic drawings show in FIG. 1 a close view of an inflorescence, and in FIG. 2 a whole flowering plant.

DETAILED BOTANICAL DESCRIPTION

The plant descriptions and measurements were taken in Gilroy, Calif. in April 2021. The plants were approximately 4 months old and were growing in 14 inch pots, three plants per pot, in a greenhouse. Color references are made to The Royal Horticultural Society Colour Chart (RHS) 2001.

TABLE 1

DIFFERENCES BETWEEN THE NEW VARIETY 'LANZ0039' AND A MOST SIMILAR VARIETY

| | 'LANZ0039' | 'LANZ0030', U.S. Plant Pat. No. 32,195 |
|---|---|---|
| Branching: | Heavily | Moderate |
| Umble size: | Medium | Larger |
| Plant size: | Smaller and semi-upright | Larger and spreading |

Plant:

*Form, growth and habit.*—Semi-woody, grown as an annual or perennial; vigorous semi-upright. habit; very well branched.

*Plant height.*—15 cm.

*Plant height* (*inflorescence included*).—17 cm.

*Plant width.*—38 cm.

Foliage:

*Type.*—Opposite.

*Immature, leaf color, upper surface.*—Closest to RHS137A.

*Lower surface.*—Closest to RHS 137C.

*Mature, leaf color, upper surface.*—RHS 147A.

*Lower surface.*—Closest to RHS 137B.

*Length.*—5.9-8.0 cm.

*Width.*—3.8-4.7 cm.

*Shape.*—Ovate.

*Base shape.*—Rounded to attenuate.

*Apex shape.*—Acute.

*Margin.*—Serrate.

*Texture, upper.*—Hairy.

*Texture, Lower surface.*—Hairy.

*Pattern of veining.*—Pinnate.

*Petioles color.*—RHS 145A.

*Petioles length.*—1.4-3.2 cm.

*Diameter of petiole.*—01.5 cm.

*Texture* (*upper and lower surface*).—Very short hairs.

Stem:

*Color of stem.*—RHS 137D.

*Length of stem.*—10.0-16.0 cm.

*Diameter.*—0.2-0.3 cm.

*Length of internodes.*—1.6-4.0 cm.

*Texture.*—Some hairs.

Inflorescence:

*Type.*—Umbel like, flattened semi-sphere the florets are sessile on an ovate receptacle.

*Blooming habit.*—Flowers continuously from spring through fall.

*Number of open flowers per inflorescence.*—About 28.

*Quantity of inflorescences per plant.*—About 35.

*Lastingness of individual blooms on the plant.*—About 3 weeks (depending on temperatures).

*Fragrance.*—Slightly spicy.

*Umbel horizontal diameter.*—3.5-3.9 cm.

*Umbel vertical height.*—1.9 cm.

*Peduncle color.*—RHS 145A.

*Length of peduncle.*—1.7-3.1 cm.

*Peduncle diameter.*—0.15 cm.

*Texture.*—Some hairs.

Flower:

*Floret form.*—Corolla salver-shaped to shallow cup-shaped, with a relatively long tube at the base; each flower subtended by a single bract.

*Length of floret.*—1.2 cm.

*Width of floret.*—0.8 cm.

*Depth of floret.*—0.4 cm.

*Young floret, color upper surface.*—RHS 14A.

*Young floret, color lower surface.*—RHS 14D with tones of RHS 170B.

*Mid age floret, color upper surface.*—Closest to RHS 26A with tones of RHS 14B.

*Mid age floret, color lower surface.*—RHS 170A and RHS 14C.

*Mature florets, color upper surface.*—RHS 169B and RHS 26A.

*Mature floret, color lower surface.*—RHS 14D and RHS 168C.

*Apex shape.*—Obtuse.

*Degree of lobation.*—Moderate.

*Margin.*—Entire.

*Base.*—Fused.

*Texture, upper surface.*—Smooth.

*Lower surface.*—Smooth.

*Tube, color outer surface.*—Closest to RHS 11C.

*Tube, color inner surface.*—Closest to RHS 16C.

*Tube, length.*—1.1 cm.

*Tube, diameter* (*at opening*).—0.15 cm.

*Tube, texture outer surface.*—Smooth.

*Inner surface.*—Very small hairs.

Bud (just before opening):

*Color.*—RHS 171C.

*Length.*—0.9 cm.

*Width.*—0.3 cm at the apex.

*Shape.*—Tubular with a flared apex.

Bract:

*Color.*—Closest to RHS 137C.

*Length.*—0.9 cm.

*Diameter.*—0.2 cm.

*Texture, upper surface.*—Small hairs.

*Lower surface.*—Small hairs.

Calyx:

*Number of sepals.*—5, fused sepals forming a short tube around the base of the floret.

*Color of sepals.*—RHS 145B.

*Length of sepals.*—0.25 cm.

*Width of sepals.*—0.15 cm.

*Apex shape.*—Obtuse.

*Apex Margins.*—Entire.

*Texture, outer surface.*—Small hairs.

*Inner surface.*—Smooth.

Reproductive organs:

*Gynoecium.*—

*Pistil quantity.*—One.

*Length.*—0.35 cm.

*Style color.*—RHS 150D.

*Style length.*—0.2 cm.

*Stigma color.*—RHS 144A.

*Ovary color.*—RHS 144A.

*Ovary length.*—0.1 cm.

*Ovary diameter.*—0.1 cm.

*Androecium.*—

*Stamen quantity.*—4.

*Color of filaments.*—RHS 159D.

*Length filaments.*—0.05 cm.

*Anther color.*—RHS 4C.

*Length of anthers.*—0.1 cm.
*Color of pollen.*—RHS 4D.
*Pollen amount.*—Scant.
*Fertility/seed set.*—Low.
*Disease/pest resistance.*—Has not been determined to date.

What is claimed is:

1. A new and distinct variety of *Lantana* plant named 'LANZ0039' substantially as illustrated and described herein.

* * * * *